Nov. 8, 1949. H. C. SWIM Plant Pat. 896
ROSE PLANT
Filed April 12, 1948
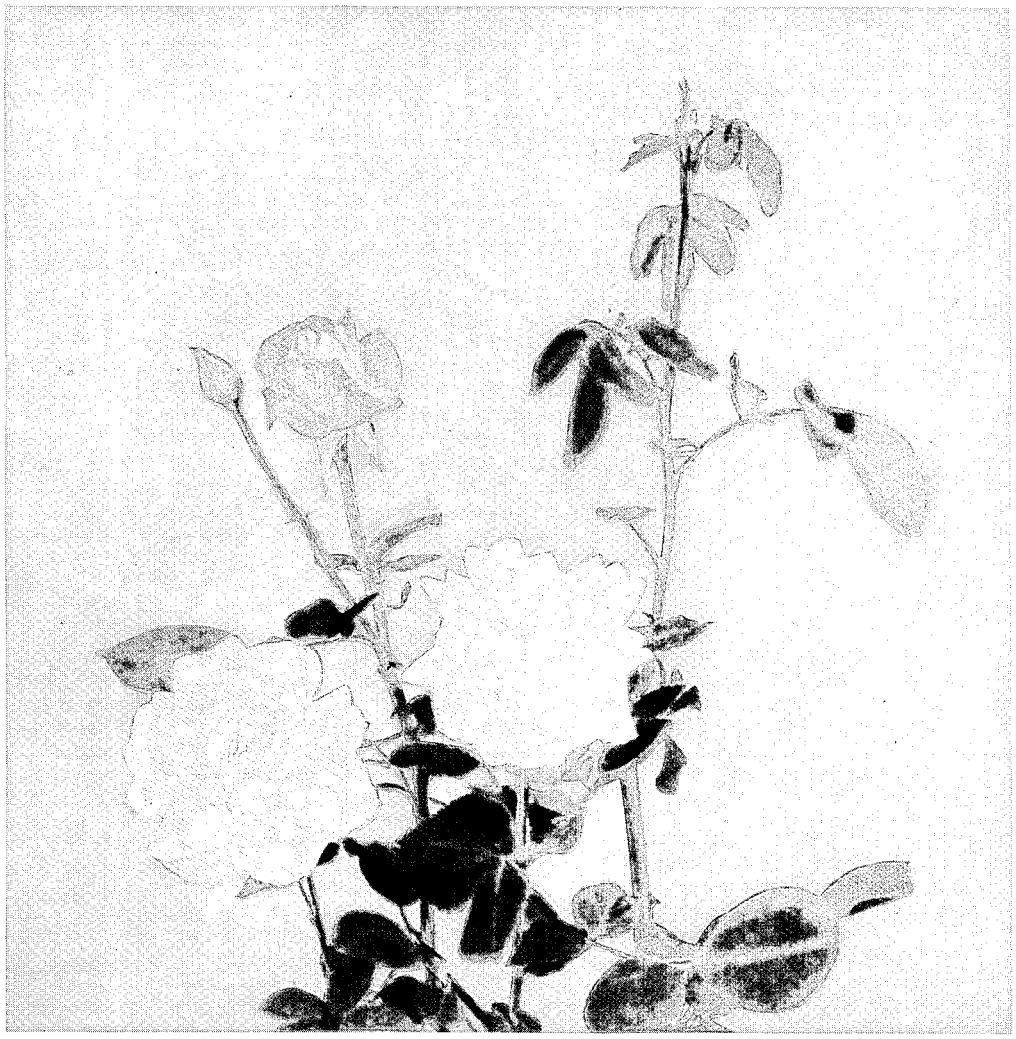
Inventor
H. C. Swim
By Robb & Robb
Attorneys Patented Nov. 8, 1949

Plant Pat. 896

UNITED STATES PATENT OFFICE

896

ROSE PLANT

Herbert C. Swim, Ontario, Calif., assignor to Armstrong Nurseries, Inc., Ontario, Calif., a corporation of California Application April 12, 1948, Serial No. 20,530

1 Claim. (Cl. 47—61)

The present invention relates to a new and distinct variety of rose plant resulting from the cross of two known varieties "Crimson Glory" and "Texas Centennial," with the objective of combining as many of the desirable qualities of both parent varieties as possible.

This new variety proves to be distinct from any other rose now available in commerce and the dominating points of distinction may be listed as follows:

(1) The attractive red color intermediate in shade between the flower color of its two parent varieties.

(2) A penetrating tea fragrance distinct from the fragrance of either of its parents.

(3) A tall growing, free-branching plant producing long stems with usually but a single flower to a stem making the variety desirable as not only a decorative plant for the garden but for cut flowers as well.

(4) Flower petals with heavy substance giving the flower improved lasting qualities when used as a cut flower.

It is distinct from its seed parent "Crimson Glory," Plant Patent No. 105, in the following respects:

(1) Whereas this new variety is tall and upright in habit of growth, its parent, "Crimson Glory," is low and spreading.

(2) The color of the flower is a lighter shade of red than those produced by the variety "Crimson Glory."

(3) The flowers of this new variety are produced on long stems whereas those of "Crimson Glory" are produced on relatively short stems.

(4) This new variety has fewer thorns than "Crimson Glory."

This new variety of rose differs from its pollen parent, "Texas Centennial," Plant Patent No. 162, as follows:

(1) Whereas this new variety is popularly classed as a deep red, its pollen parent is usually described as a deep pink or light red.

(2) This new variety produces canes more slender in habit than those of its pollen parent.

(3) Whereas this new variety is properly classed as a decorative type rose, "Texas Centennial" is more correctly described as an exhibition type.

(4) The leaflets of this new variety are characteristically oval in shape whereas those of "Texas Centennial" are ovate to ovate-lanceolate.

Asexual reproduction shows that these characteristics hold true through succeeding propagations.

The accompanying illustration shows specimens of the flowers (much reduced in size) at different stages of development from bud to full bloom, and young and mature specimens of foliage of this new variety.

The following is a detailed description of the new variety, all references to color being in accordance with the R. F. Wilson's Horticultural Colour Chart, except where indicated to be in accordance with Ridgway's Color Standards and Nomenclature:

Type: Bush; outdoor; for cut flowers and garden decoration.

Class: Hybrid Tea.

Breeding: Seedling.

*Seed parent.*—"Crimson Glory."

*Pollen parent.*—"Texas Centennial."

Propagation: Holds its distinguishing characteristics through succeeding propagations by budding.

*Flower*

Locality where grown: Ontario, California.

Flowers borne: Singly, occasionally two, to stem; occasionally in irregular cluster; on strong, long stems.

Quantity of bloom: Free; outdoors.

Continuity: More or less continuous during growing season.

Fragrance: Penetrating to strong; tea.

Bud:

*Peduncle.*—Medium to long; heavy; erect; almost smooth; few gland-tipped cilia and hairs. *Color*—Rainette Green, Plate XXXI (Ridgway), becoming washed on side exposed to sun with Prussian Red, Plate XXVII (Ridgway).

*Before calyx breaks.*—*Size*—medium to large. *Form*—long, pointed to ovoid; with foliaceous appendages, tomentum, gland-tipped cilia on the surface of the bud; with slender, much cut foliaceous parts extending beyond the tip of the bud equal to ¼ to ½ of its length.

*As calyx breaks.*—Color—near Chrysanthemum Crimson, Plate 824, page 169. *Sepals*—inner surface: With fine, woolly tomentum. When the margin of a sepal is not covered by the margin of an adjacent sepal, it has woolly tomentum and stipitate glands on both margins; but if margin is covered with adjacent sepals, the margin so covered has only woolly tomentum.

*As first petal opens.*—*Size*—medium to large. *Form*—long; pointed to urn shape. *Color*—outside: Cardinal Red, Plate 822/1, page 168, washed with Chrysanthemum Crimson, Plate 824/1, page 169; inside: near Currant Red, Plate 821/1 page 167, with a small spot of Lemon Yellow, Plate 4, page 4, at base of petal.

*Opening.*—Opens up well. Is not prevented from opening by cold, hot, wet or dry weather.

Bloom: Size, when fully open—medium to large; 3½ inches to 4½ inches.

*Petalage.*—Double; from 24 to 30 petals, arranged regularly, usually with three to five petaloids.

*Form.*—Full high center at first; becoming flat to open; petals remaining at first loosely rolled outward; later, at maturity, loosely rolled outward.

Petals: Thick; leathery; with inside velvety and outside satiny.

*Shape.*—Outside: round; scalloped with apex flat, with one to three notches. Intermediate: obovate, occasionally mucronate; scalloped with one to three notches. Inside: obovate cuneate; scalloped irregular with one to two notches.

*Color.*—Colors may be modified by being shaded or washed with other colors.

This description of a newly opened flower was made from a rose grown outdoors in the month of October, at Ontario, California:

*Color.*—*Outside petal*—outside surface: near Cardinal Red, Plate 822/3, page 168, with a very small spot of Aureolin, Plate 3/2, page 3, at base of petal; inside surface: near Cardinal Red, Plate 822/2, page 168, shading through Crimson, Plate 22, page 22, with a spot of Lemon Yellow, Plate 4/3, page 4, at base of petal. *Intermediate petal*—outside surface: near Cardinal Red, Plate 822/3, page 168, with a very small spot of Aureolin, Plate 3/2, page 3, at base of petal; inside surface: near Cardinal Red, Plate 822/2, page 168, shading through Crimson, Plate 22, page 22, with a spot of Lemon Yellow, Plate 4/3, page 4, at base of petal. *Inner petal*—outside surface: near Cardinal Red, Plate 822/3, page 168, with a very small spot of Aureolin, Plate 3/2, page 3, at base of petal; inside surface: near Cardinal Red, Plate 822/2, page 168, shading through Crimson, Plate 22, page 22, with a spot of Lemon Yellow, Plate 4/3, page 4, at base of petal.

This description was made from a rose that was open for three days outdoors in the month of October, at Ontario, California.

*Color.*—*Outside petal*—outside surface: near Rose Bengal, Plate 25, page 25, with a very small spot of Aureolin, Plate 3/1, page 3, at base of petal; inside surface: near Tyrian Purple, Plate 727, page 159, with a spot of Lemon Yellow, Plate 4/1, page 4, at base of petal. *Inside petal*—outside surface: near Rose Red, Plate 724/3, page 158, with a small spot of Aureolin, Plate 3/1, page 3, at base of petal; inside surface: near Rose Red, Plate 724/1, page 158, with a spot of Lemon Yellow, Plate 4/1, page 4, at base of petal.

*General color effect.*—Newly opened flower—near Cardinal Red, Plate 822/2, page 168. Three days open—near Rose Red, Plate 724/1, page 158.

*Behavior.*—Drop off cleanly; fading only slightly purple; affected by hot, dry weather by fading to a lighter shade.

*Flower longevity.*—On bush in garden—four days in October. Cut roses grown outdoors kept at living-room temperatures—three days in October.

*Reproductive organs*

Stamens: Medium to many, usually about 50; arranged regularly about pistils.

Filaments: Medium length; from 5 to 9 mm. long; most with anthers. *Color*—near Poppy Red, Plate 16/1, page 16.

Anthers: Large; all open at once. *Color*—Saffron Yellow, Plate 7/2, page 7.

Pollen: Abundant. *Color*—near Majolica Yellow, Plate 09/1, page 102.

Pistils: Medium in number, usually about 40.

Styles: Uneven; medium to long; from 5 to 10 mm. in length; medium in caliper; loosely bunched. *Color*—near Sulphur Yellow, Plate 1/3, page 1, at base shading to Cardinal Red, Plate 822, page 168, near stigma.

Stigma: *Color*—translucent near Mimosa Yellow, Plate 602/3, page 143.

Ovaries: Some protruding from calyx.

Hips: Globular; moderately rough; walls thick, fleshy. *Color*—from Olive Yellow, Plate XXX (Ridgway) to Yellow Ocher, Plate XV (Ridgway).

Sepals: Falling soon; curled. *Color*—inside: near Tawny Olive, Plate XXIX (Ridgway); outside: near Tawny Olive, Plate XXIX (Ridgway).

Seeds: Few to many; medium size, usually from 5 to 12 in number.

*Plant*

Foliage:

*Leaves.*—Compound of 5 to 7 leaflets; normal to abundant; medium size; heavy; semi-glossy.

*Leaflets.*—Shape—oval with apex mucronate. Base—round. Margin—simply, sometimes doubly, serrate.

*Color.*—*Mature*—upper surface: near Varley's Green, Plate XVIII (Ridgway); under surface: near Mytho Green, Plate XLI (Ridgway). *Young*—upper surface: near Dark Corinthian Purple, Plate XXXVIII (Ridgway); under surface: near Mineral Red, Plate XXVII (Ridgway).

*Rachis.*—Medium heavy. Upper side—grooved with few stipitate glands. Under side—smooth with only a very few stipitate glands.

*Stipules.*—Medium to long; narrow to medium in width; with short points, turning out at an angle of more than 90°.

*Disease.*—Relatively resistant to mildew in its color class.

Growth:

*Habit.*—Bushy; upright; much branched.

*Growth.*—Vigorous.

*Canes.*—Moderately heavy.

*Main stems.*—Color—near Light Cress Green, Plate XXXI (Ridgway). *Large prickles*—several; medium to long; hooked downward; with long, narrow base. Color—near Tawny Olive, Plate XXIX (Ridgway),

*Small prickles*—few. *Color*—near Tawny Olive, Plate XXIX (Ridgway). *Hairs*—none.

*Branches.*—Color near Light Cress Green, Plate XXXI (Ridgway). *Large prickles*—several; medium in length; hooked downward; with long, narrow base. Color—near Auburn, Plate II (Ridgway). *Small prickles*—few. Color—near Auburn, Plate II (Ridgway). *Hairs*—None.

*New shoots.*—Color—near Absinthe Green, Plate XXXI (Ridgway) washed with Mineral Red, Plate XXVII (Ridgway). *Large prickles*—few; medium in length; straight or sometimes hooked downward; with short, narrow base. Color—near Mineral Red, Plate XXVII (Ridgway). *Small*

*prickles*—few. Color—occasionally translucent to Mineral Red, Plate XXVII (Ridgway). *Hairs*—none.

I claim:

A new and distinct variety of rose plant, characterized as to novelty by its tall, upright and free-branching habit of growth producing long stems with usually but a single flower to a stem; the red color of the flowers with petals of heavy substance; the penetrating tea fragrance of its blooms; the oval shape of its leaflets, and small number of thorns, substantially as shown and described.

HERBERT C. SWIM.

No references cited.